(12) United States Patent
Lewalter et al.

(10) Patent No.: US 8,576,988 B2
(45) Date of Patent: Nov. 5, 2013

(54) DISTRIBUTED X-RAY SOURCE AND X-RAY IMAGING SYSTEM COMPRISING THE SAME

(75) Inventors: Astrid Lewalter, Aachen (DE); Rainer Pietig, Malsch (DE); Wolfgang Chrost, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 13/393,835

(22) PCT Filed: Sep. 13, 2010

(86) PCT No.: PCT/IB2010/054113
§ 371 (c)(1),
(2), (4) Date: Aug. 14, 2012

(87) PCT Pub. No.: WO2011/033439
PCT Pub. Date: Mar. 24, 2011

(65) Prior Publication Data
US 2012/0300901 A1    Nov. 29, 2012

(30) Foreign Application Priority Data
Sep. 15, 2009  (EP) .................................... 09170298

(51) Int. Cl.
*H01J 35/08* (2006.01)
*H01J 35/28* (2006.01)

(52) U.S. Cl.
USPC ............................ 378/126; 378/134; 378/143

(58) Field of Classification Search
USPC ............ 378/4–20, 91, 94, 98, 98.6, 119, 121, 378/125, 126, 131, 134–137, 143, 144
See application file for complete search history.

(56) References Cited

U.S. PATENT DOCUMENTS

| 4,287,420 | A  | * | 9/1981  | Yamamura et al. | ............ 378/41 |
| 5,703,924 | A  | * | 12/1997 | Hell et al. | ...................... 378/136 |
| 2003/0198318 | A1 | * | 10/2003 | Price et al. | .................... 378/122 |
| 2006/0072801 | A1 |   | 4/2006  | Bernard Deman et al. | |
| 2006/0274889 | A1 |   | 12/2006 | Lu et al. | |
| 2009/0185655 | A1 | * | 7/2009  | Koken et al. | .................... 378/11 |

FOREIGN PATENT DOCUMENTS

EP    0062219 A2   10/1982
WO    2009112986 A2   9/2009

* cited by examiner

*Primary Examiner* — Anastasia Midkiff

(57) ABSTRACT

A distributed X-ray source (3) and an imaging system (1) comprising such an X-ray source (3) are proposed. The X-ray source (3) comprises an electron beam source arrangement (19) and an anode arrangement (17). The electron beam source arrangement (19) is adapted to emit electron beams (24) towards at least two locally distinct focal spots (27) on the anode arrangement (17). Therein, the X-ray source is adapted for displacing the anode arrangement (17) with respect to the electron beam source arrangement (19). While the provision of a plurality of focal spots allows acquisition of projection images under different projection angles thereby allowing reconstruction of three-dimensional X-ray images e.g. in tomosynthesis application, a displacement motion of the anode arrangement (17) with respect to the electron beam source arrangement (19) may allow for distributed heat flux to the anode arrangement thereby possibly reducing cooling requirements.

14 Claims, 3 Drawing Sheets

DISTRIBUTED X-RAY SOURCE AND X-RAY IMAGING SYSTEM COMPRISING THE SAME

FIELD OF THE INVENTION

The present invention relates to a distributed X-ray source which is adapted to emit X-ray beams from locally distinct focal spots. Furthermore, the present invention relates to an X-ray imaging system, particularly a medical imaging system, comprising such distributed X-ray source.

BACKGROUND OF THE INVENTION

X-ray imaging systems may be utilized for various applications both in a medical and in a non-medical field. For example, medical X-ray imaging systems may include general radiological, mammography, X-ray C-arm, tomosynthesis and computed tomography imaging systems. Such imaging systems may be adapted to create images or views of a part of a patient based on an attenuation of X-rays passing through the patient. Alternatively, X-ray imaging systems may be used in non-medical applications such as security screening of passenger luggage or industrial quality control.

In the following, one specific application of X-ray imaging known as tomosynthesis which may be used for example in medical X-ray mammography analysis will be described in more detail. However, it is to be noted that the present invention is not limited to such application.

In tomosynthesis multiple X-ray projections may be taken of a same region of interest, but from different angles, in order to provide volumetric (3D) or quasi-volumetric (quasi-3D) information of the imaged object after a mathematical reconstruction process of acquired image data. Generally, with tomosynthesis, a total angular range of an acquired data set is limited. This may mean that not a full 3D reconstruction of the region of interest can be obtained but a depth resolution may be much lower than a 2D resolution of originally acquired individual X-ray projections, and it may depend on the number of X-ray projections and the total angular range for which X-ray projections have been acquired.

A conventional system setup for X-ray tomosynthesis for medical imaging comprises a conventional X-ray tube that is sequentially moved to different locations, taking a projection image of the same region of interest at each location with a detector positioned on an opposite site of the object. A path described by the X-ray tube may be straight, a circular segment or any other curve within a limited total angular range. The X-ray tube used in such conventional system setup for X-ray tomosynthesis may usually be a standard X-ray tube with a rotating anode because a maximum possible power rating of a an X-ray tube with a stationary anode may not be high enough in order to obtain a required number of images within a given period of time, e.g. within several seconds.

However, a standard X-ray tube with a rotating anode, as it is used e.g. for mammography, may be very large and heavy. Therefore, it may be very difficult to move such X-ray tube through a number of different image acquiring locations. Two approaches are generally pursued, however each with its own disadvantages:

(a) step and shoot: This may require frequent and rapid acceleration and deceleration of the entire X-ray tube, which might lead to vibration of the total X-ray imaging system, possibly deteriorating an image quality due to motion artefacts;

(b) continuously moving the X-ray tube: The moving X-ray source (and therefore the continuously moving focal spot) may blur the acquired X-ray projection images.

In any of these cases, it may not be possible to move the large and heavy X-ray tube very fast such that a total examination time may be quite long. In case of tomosynthesis for mammography this may result in considerable patient discomfort in addition to a risk of generating motion artefacts for example due to breathing.

If, as an alternative, multiple stationary X-ray tubes were used instead of a single moving X-ray tube, standard rotating anode tubes might be too large to be mounted side by side. Also, a resulting power consumption and cost price of such system might be too high for a commercial medical imaging system.

As a further alternative, small conventional X-ray tubes with a stationary anode might be used. However, in such X-ray imaging system, required power rating might not be reached in order to obtain a required number of images within a reasonably short time.

Again, a long total examination time may lead to considerable patient discomfort.

SUMMARY OF THE INVENTION AND EMBODIMENTS THEREOF

There may be a need for an improved X-ray imaging system that may overcome at least some of the above-mentioned deficiencies of conventional systems. Particularly, there may be a need for an X-ray imaging system that may avoid vibrations due to motion of a large and heavy X-ray tube, focus blur and/or power limitations.

According to a first aspect of the present invention, a distributed X-ray source is proposed. The X-ray source comprises an electron beam source arrangement and an anode arrangement. The electron beam source arrangement is adapted to emit electron beams towards at least two locally distinct focal spots on the anode arrangement. The X-ray source is adapted for displacing the anode arrangement with respect to the electron beam source arrangement.

A basic idea underlying the present invention according to this first aspect is to provide an X-ray source which is able to emit X-ray beams from a plurality of locally distributed focal spots on an anode arrangement with a high X-ray power. For this purpose, the electron beam source arrangement may comprise one or more electron beam emitters, also referred to as electron emission cathodes. Preferably, the number of electron beam emitters may be equal to the number of focal spots arranged on the anode arrangement such that each focal spot may receive an electron beam from a specific associated electron beam emitter. At least two focal spots are provided on the anode arrangement, however it is preferred to provide a larger plurality of focal spots, e.g. more than 5 focal spots, preferably more than 10 focal spots on the anode arrangement, wherein the focal spots may be arranged at substantial distances of e.g. several centimeters with respect to each other. From each of the focal spots, an X-ray beam may be emitted which allows generating X-ray projection images of a region of interest from different positions and under different angles.

A substantial feature of the proposed distributed X-ray source may be seen in the fact that the anode arrangement may be displaced with respect to the electron beam source arrangement. As a result of such displacement, an electron beam emitted from the electron beam source arrangement does not stationarily impact onto the anode arrangement at a same surface of the anode arrangement but, due to the displacing of the anode arrangement, a surface area of the anode arrangement onto which the electron beam impacts may change over time. Accordingly, thermal energy introduced into the anode arrangement due to impacting electrons may be spread over a larger surface area thereby possibly preventing local overheating. As a result thereof, the power of the impacting electron beam, i.e., the flow of electrons, may be increased compared with a case of a stationary anode arrangement. Thus, the proposed distributed X-ray source enables X-ray imaging with multiple projections, like e.g. in tomosynthesis, with a considerable decrease of total examination time, thereby possibly significantly improving patient comfort for example in the case of tomosynthesis for mammography.

It is to be noted that herein, the term "displacing" may be interpreted in that the anode arrangement not simply rotates like in conventional rotating anode X-ray tubes but the entire anode arrangement is displaced in a non-rotational movement with respect to the electron beam source arrangement. In other words, a center of gravity of the anode arrangement may be moved with respect to the electron beam source arrangement. The displacing motion may be effected by any kind of actuator such as a motor forcibly acting on the anode arrangement. In order to prevent or reduce vibration induced by the displacement motion, the anode arrangement may be connected to a damping means or a counter-weight means. The electron beam source arrangement may be fixed within the distributed X-ray source.

The anode arrangement may be provided as a single unit made of a suitable material for emitting X-rays upon incidents of an electron beam or on which areas made of such suitable material are provided for each of the focal spots. Alternatively, the anode arrangement may be composed of a plurality of separate anode sub-arrangements such that a focal spot can be generated on each of the anode sub-arrangements. The sub-arrangements may be mechanically interconnected. The anode arrangement as an entity or each of the anode sub-arrangements may be mounted in such a way that electrons emitted from the electron beam source arrangement are accelerated and focused towards a respective associated focal spot.

According to an embodiment, the proposed distributed X-ray source is adapted for displacing the anode arrangement with respect to the electron beam source arrangement in a way such that during the displacement movement a position of the focal spots remains stationary. In other words, while the entire anode arrangement may be displaced during operation of the distributed X-ray source, it should be arranged and displaced in a way such that a position of a focal spot, i.e. the position, where an electron beam from the electron beam source arrangement impacts onto an X-ray generating surface of the anode arrangement, remains unchanged. In case the plurality of focal spots is arranged in a plane, this may for example be obtained by displacing the anode arrangement parallel to such plane. In other words, the anode arrangement may be displaced such that a surface of the anode arrangement including an active focal spot remains at the same position with respect to the electron beam source arrangement and at a same angle with respect to a direction of an impacting electron beam.

According to an embodiment, the anode arrangement shall be displaced with respect to the electron beam source arrangement in a back-and-forth movement along a linear path, an arcuate path or a curvilinear path. For example, when the anode arrangement is designed such that all of the focal spots are arranged within a same plane, it may be advantageous to displace the anode arrangement during operation of the distributed X-ray source in a back-and-forth movement along a linear path within this plane. Alternatively, when the anode arrangement is designed such that the multiplicity of focal spots is arranged along an arcuate surface, it may be advantageous to displace the anode arrangement during operation of the distributed X-ray source in a pivoting motion along an arcuate path which preferably coincides with the arcuate surface of the anode arrangement. Thereby, it may be achieved that during the displacement, both a distance and an angular position relationship of an anode arrangement surface including the active focal spots remain stationary.

According to an embodiment, the distance between adjacent focal spots on the anode arrangement is at least 5 mm, preferably at least 1 cm and more preferred at least 2 cm; for example, the distance may be in a range of 0.5 to 10, preferably in a range of 1 to 5 cm. For example, for an application of the proposed distributed X-ray source in a medical X-ray imaging system which may be used for tomosynthesis, the focal spots may be arranged at such positions and with such distances in between such that X-ray beams emitted from the focal spots and collimated towards a detector may be transmitted through an object to be examined under substantially differing angles. Accordingly, X-ray projection images acquired under such differing projection angles may be used to derive a volumetric image of the examined object.

According to an embodiment, the electron beam source arrangement is adapted for fast switching ON and OFF emitted electron beams. Such fast switching may be achieved e.g. by providing a chargeable switching grid between the electron beam source arrangement and the anode arrangement wherein the switching grid may be charged to an electrical potential such as to prevent the emission of an electron beam from the electron beam source arrangement towards the anode arrangement. "Fast switching" may mean that the electron beam source arrangement may switch between an ON-state and OFF-state and vice versa in less than 100 µs, preferably less than 1 µs.

According to an embodiment, the electron beam source arrangement comprises a plurality of electron beam emitters, each emitter being adapted for emitting an electron beam towards one associated focal spot on the anode arrangement. In other words, the number of electron beam emitters may be equal to the number of focal spots such that each focal spot may be irradiated by its own associated electron beam emitter.

According to an embodiment, the distributed X-ray source is adapted for switching ON and OFF electron beams emitted from different focal spots independently from each other. For example, each electron emitter may be provided with its own associated switching grid. Accordingly, the distributed X-ray source may be operated such that, at a given point in time, only one of the electron beam emitters is switched ON, i.e. emits an electron beam towards an associated focal spot on the anode arrangement thereby emitting X-rays from the irradiated focal spot. The other electron beam emitters may be switched OFF at that point in time. Successively, another one of the electron beam emitters may be switched ON thereby activating another focal spot for emitting X-rays from a different location and possibly in a different direction. Sequentially, all of the focal spots may be activated by switching on their associated electron beam emitter.

According to an embodiment, the electron beam source arrangement is provided with one or more cold field emission cathodes, one or more photoelectric cathodes and/or one or more low work function cathodes. Such cathodes may have a higher potential for fast switching, miniaturization and/or low standby power consumption compared to e.g. standard thermionic X-ray cathodes due to a lack of required filament heating. A cold field emission cathode may e.g. be based on carbon nanotubes or other forms of carbon or some other form of field emitter structures.

According to an embodiment, the anode arrangement is provided with a sheet material such that electrons emitted from the electron source arrangement impinge on one surface of the sheet material. Furthermore, the anode arrangement is provided with an active cooling arranged on an opposite side of the sheet material. In other words, the anode arrangement may comprise a thin sheet which at least on the side onto which electrons from the electron source arrangement impinge comprises a material for emitting X-rays upon incidents of an electron beam. On an opposite side of such sheet, a cooling arrangement such as a liquid coolant arrangement may be provided. Due to a thinness of the sheet and possibly due to a good thermal conductivity of the sheet material, an effective cooling of the areas of the focal spots may be provided. Thus, the focal spots in the anode arrangement may be irradiated with a high electron beam power without overheating.

According to a second aspect of the present invention, an X-ray imaging system is proposed. The X-ray imaging system comprises a distributed X-ray source as described above with respect to the first aspect of the invention. The distributed X-ray source is arranged on a first side of an examination space. Furthermore, the X-ray imaging system comprises a detector which is arranged on a second side opposite to the first side of the examination space. Therein, the distributed X-ray source is adapted such that X-rays emitted from each of the focal spots cross the examining space at different angles.

Accordingly, with the emitted X-rays crossing the examination space under different angles, different X-ray projection images of an object accommodated within the examination space may be obtained under different projection angles.

For example, the X-ray imaging system may be adapted to emit X-rays sequentially from each of the focal spots for projecting a region of interest in the examination space under different angles onto the detector and to acquire a plurality of respective projection images with the detector. Based on the acquired projection images, a three-dimensional image of the region of interest may be calculated.

For example, in order to collimate X-rays emitted from at least one of the focal spots into X-ray channels for projecting the region of interest onto the detector, a collimator may be provided. Such collimator may be arranged between the distributed X-ray source and the region of interest. For example, the collimator may comprise apertures at multiple positions such that X-rays emitted from a focal spot within the distributed X-ray source may pass through such apertures thereby forming X-ray channels having a restricted angular extent. Each of the X-ray channels may be used for projecting an X-ray projection image onto the detector.

The proposed X-ray imaging system may be suitably adapted for medical imaging, such as tomosynthesis for mammography or for arms and legs or within preclinical tomosynthesis systems. Alternatively, the X-ray imaging system may be comprised in a high throughput baggage scanning system.

It has to be noted that aspects and embodiments of the present invention have been described with reference to different subject-matters. In particular, some embodiments have been described with reference to the distributed X-ray source whereas other embodiments have been described with respect to the X-ray imaging system. However, a person skilled in the art will gather from the above and the following description that, unless other notified, in addition to any combination of features belonging to one type of subject-matter also any combination between features relating to different subject-matters are considered to be disclosed with this application.

BRIEF DESCRIPTION OF THE DRAWINGS

Features and advantages of the present invention will be further described with respect to specific embodiments as shown in the accompanying figures but to which the invention shall not be limited.

FIG. 2 shows a front view of essential features of the X-ray imaging system shown in FIG. 1. Therein.

The drawings are schematically only and not to scale. Throughout the figures, similar or identical features are referenced with corresponding reference signs.

DETAILED DESCRIPTION OF EMBODIMENTS

Figure 1:
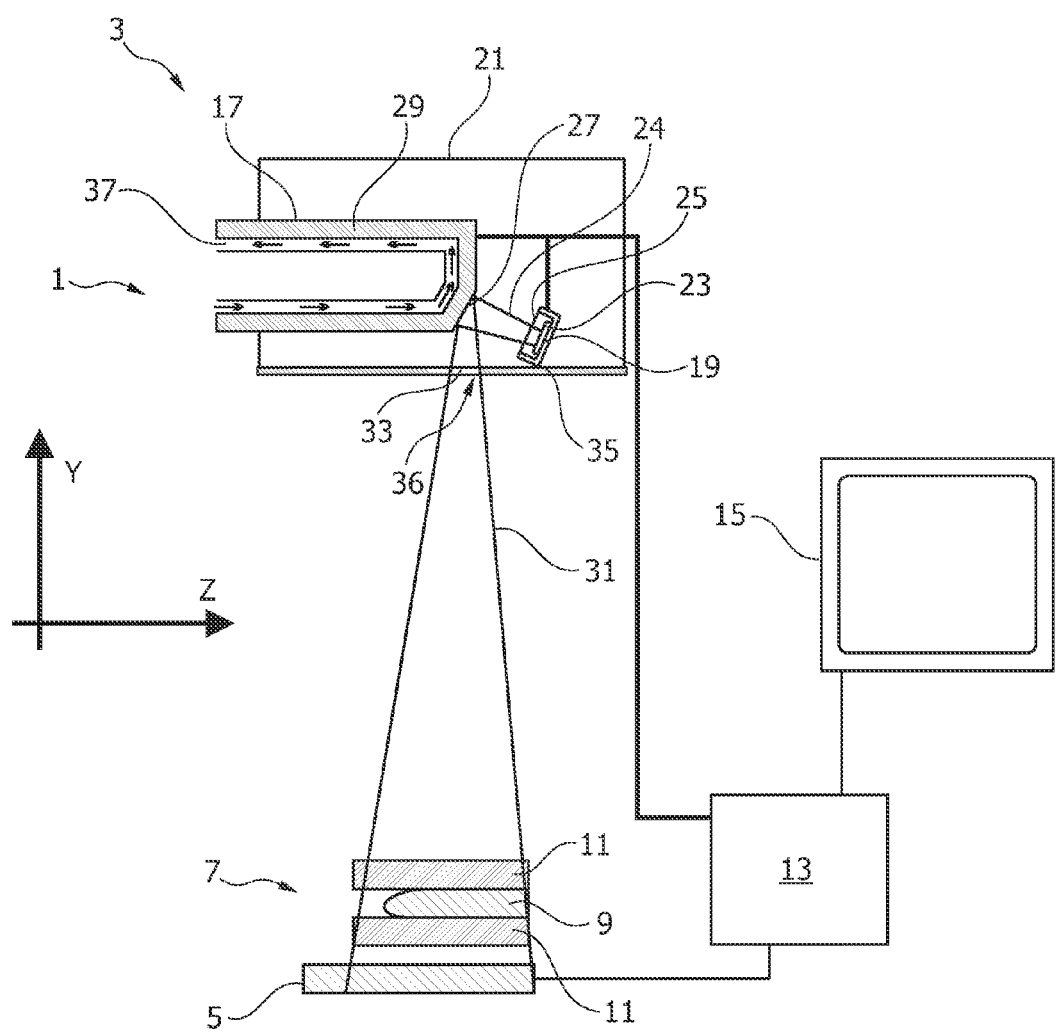
FIG. 1 shows a side view of an X-ray imaging system comprising a distributed X-ray source according to an embodiment of the present invention.

FIG. 1 shows an X-ray imaging system according to an embodiment of the present invention in a side view, i.e. in the y-z-plane. The X-ray imaging system 1 comprises a distributed X-ray source 3 in accordance with an embodiment of the present invention, and an X-ray detector 5. The distributed X-ray source 3 and the detector 5 are arranged at opposite sides of an examination space 7. In the specific embodiment shown in FIG. 1, the X-ray imaging system 1 is realized as a tomosynthesis mammography system, wherein an object 9 to be examined may be a female breast which is held between two X-ray-transmitting plates 11. The distributed X-ray source 3 and the detector 5 are connected to a control 13 which may be adapted to both, control an operation of the X-ray source 3 and to receive and process data obtained by the detector 5. From such data, the control 13 may calculate three-dimensional images which may then be displayed on a display 15.

The distributed X-ray source 3 comprises an anode arrangement 17 and an electron beam source arrangement 19 enclosed by a housing 21. The electron beam source arrangement 19 comprises a plurality of electron beam emitters 23 arranged linearly next to each other in an x-direction perpendicular to the image plane shown in FIG. 1. Preferably, there are as many electron beam emitters 23 as there should be projection images with one scan of the X-ray imaging system such that finally the desired three-dimensional image may be calculated from the multiplicity of projection images. A distance between adjacent electron emitters 23 may be in a range of a few centimeters such that the entire electron beam source arrangement 17 may extend e.g. over some tenth of centimeters in the x-direction. The dimension of the electron beam source arrangement 17 in x-direction may be larger than the dimension of the examined object 9.

Each electron emitter 23 may be provided for example as a cold field emission cathode in which sharp structures, which may e.g. be created by carbon nanotubes, may support an emission of electrons from an emission surface. The electron beam emitters 23 may offer fast switching, miniaturization and low power dissipation. The emitted electrons may be accelerated in an electron beam 24 towards the anode arrangement 17 due to an electric field of for example more than 20 kV applied between the electron beam source arrangement 19 and the anode arrangement 17. In order to be able to selectively switch ON or OFF any of the electron emitters 23 individually, each electron emitter 23 is provided with an associated switching grid 25. The switching grid 25 is arranged within a path of the electron beam 24 from the electron emitter 23 to the anode arrangement 17 and may be set to an electrical potential such as to selectively prevent electrons emitted from the electron emitter 23 to be accelerated towards an associated focal spot 27 on the anode arrangement 17. The switching grids 25 may be controlled by the control 13. Accordingly, each of the grids 25 may be controlled individually such that the electron beam 24 from each of the electron emitters 23 may be selectively switched ON or OFF independently from neighbouring electron beams 24.

The anode arrangement 17 is provided with a thin sheet 29. On an outside surface of the sheet 29 an area may be provided with a material such as tungsten which emits X-rays upon incidents of accelerated electron beams 24. In this area, electrons emitted from an electron emitter 23 switched in the ON-state and impacting onto the outside surface of the sheet 29 of the anode arrangement 17 may generate an X-ray beam 31. The X-ray beam may exit the housing 21 through an X-ray window 33. Furthermore, a collimator 35 having a plurality of apertures 36 may be provided for collimating the emitted X-ray beam 31 both in a z-direction and in an x-direction.

An inside surface of the sheet 29 of anode arrangement 17 may be in direct contact with an active cooling 37. The active cooling 37 may be provided as a liquid coolant system in which a coolant such as water may circulate through a conduit being in thermal contact with the inside surface of the sheet 29 of the anode arrangement 17. Thereby, thermal energy applied by electrons impinging onto the focal spots 27 and heating the anode arrangement 17 may be effectively absorbed. Due to the thinness of the sheet 29, such cooling may be very effective as it may reach close to the focal spots 27 thereby allowing to reach a high power level for the emitted X-ray beam 31.

After exiting the housing 21, the X-ray beam 31 may cross the object 9 before being detected by the detector 5. Due to X-ray attenuation within the object 9, an X-ray projection image of the object 9 may be acquired by the control 13 connected to the detector 5.

As will be described with reference to FIGS. 2a to 2f, a plurality of projection images may be acquired under different projection angles. Based on such different projection images, the control 13 may derive a three-dimensional representation of the object 9 to be displayed on the display 15.

In FIG. 2, the X-ray imaging system 1 of FIG. 1 is shown in front view, i.e. in an x-y-plane. In FIG. 2, some of the features of the X-ray imaging system shown in FIG. 1 such as the housing 21, the electron beam source arrangement 19, etc. are not shown for clarity reasons.

Figure 2A:
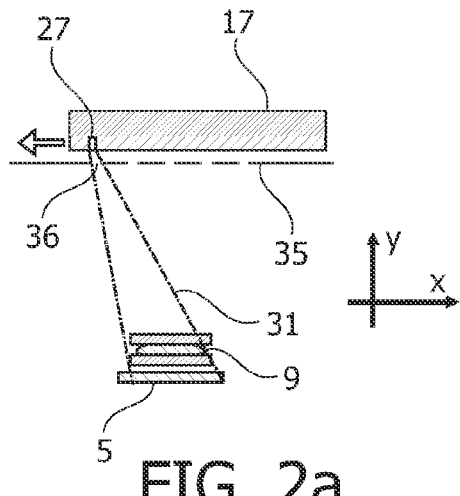
FIGS. 2a-f show subsequent steps in an operation of the X-ray imaging system.
Figure 2B:
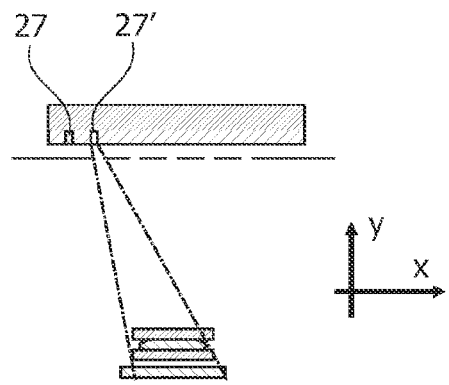

As schematically shown in FIGS. 2a and 2b, in a first image acquisition step, a first electron emitter 23 (not shown in FIG. 2) is switched ON thereby emitting electrons onto a first focal spot 27. The generated X-ray beam 31 is collimated by an aperture 36 of the collimator 35 such as to be directed towards the object 9 under a first projection angle. A first projection image may thus be acquired under such projection angle by the detector 5.

During the acquisition of the first projection image, the anode arrangement 17 is initially displaced with respect to the electron beam source arrangement 19 in the (−x)-direction as indicated by the arrow in FIG. 2a. Due to such displacement, the area irradiated by electron beam 24 emitted from the electron emitter 23, i.e. the focal spot 27, moves along the surface of the anode arrangement 17. As shown in FIG. 2b the area of the initial focal spot 27 (as shown in FIG. 2a) has moved to the left and the focal spot 27' irradiates a different area on the anode arrangement 17. Accordingly, due to the displacement of the anode arrangement 17, a heat entry to the anode arrangement 17 may be distributed over a larger surface of the anode arrangement 17 thereby possibly relaxing any cooling requirements. It is to be mentioned that the anode arrangement 17 may be displaced back and forth in a translational displacement once or several times during a time period for acquiring a respective projection image and that the anode arrangement 17 may be displaced continuously or stepwise. While the area currently irradiated by electrons moves along the surface of the anode arrangement 17 during image acquisition due to the displacement movement of the anode arrangement 17, an absolute position of the focal spot 27 remains unchanged as the location of the electron beam source arrangement 19 remains fixed within the distributed X-ray source 3. Due to such fixed location of the focal spot 27, no image blurring occurs. Furthermore, due to the thinness of the sheet 29 and the resulting low weight of the anode arrangement 17, there is no substantial risk of vibrations occurring due to the displacement of the anode arrangement 17

Figure 2C:
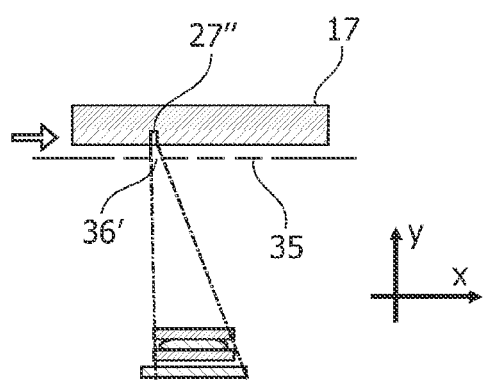
Figure 2D:
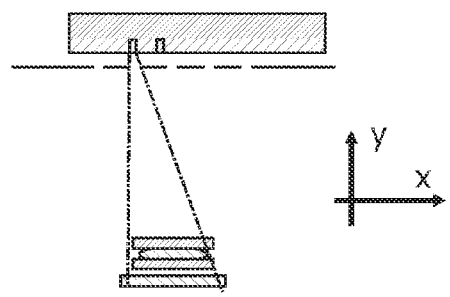

As shown in FIGS. 2c and 2d, a second projection image may be acquired by switching ON a neighbouring electron emitter 23 on the electron beam source arrangement 19 thereby generating a locally displaced focal spot 27". Again, an X-ray beam 31 emitted from the focal spot 27" may be collimated by an aperture 36' within the collimator 35 such that a second X-ray projection image may be acquired under a different observation angle. Also during this image acquisition, the anode arrangement 17 may be continuously displaced in a linear back-and-forth displacement movement as indicated by the arrow in FIG. 2c in order to spread the introduced heat over an extended surface of the anode arrangement 17.

Figure 2E:
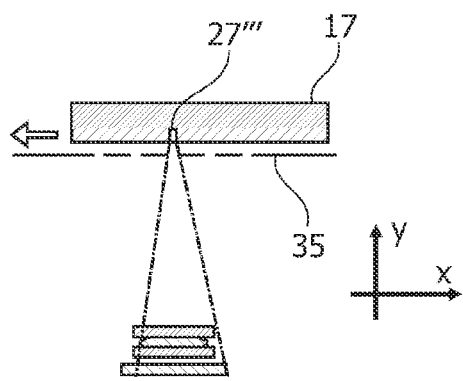
Figure 2F:
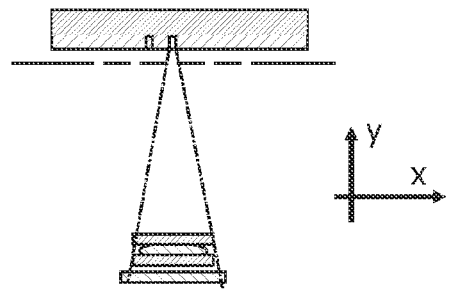

As shown in FIGS. 2e and 2f, a third projection image may be acquired again under a different observation angle by switching ON a third electron emitter 23 thereby activating a different focal spot 27'''.

In the embodiment shown in FIGS. 1 and 2, both the electron beam source arrangement 19 with the electron emitters 23 as well as the anode arrangement 17 with the plurality of focal spots 23 on its surface are provided with a linear extension in a x-direction. The linear displacement of the anode arrangement 17 during X-ray image acquisition coincides with the linear extension of the anode arrangement 17.

Further benefits may be realized if the electron beam emitters 23 may be switched ON and OFF very fast, and if the digital X-ray detector 5 offers a high frame rate. This would allow very fast "sub-image" switching between the different focal spots and thus even more increase the instantaneous power rating of the X-ray sources, thus enabling to reduce a total time required for a full scan even further.

Figure 3:
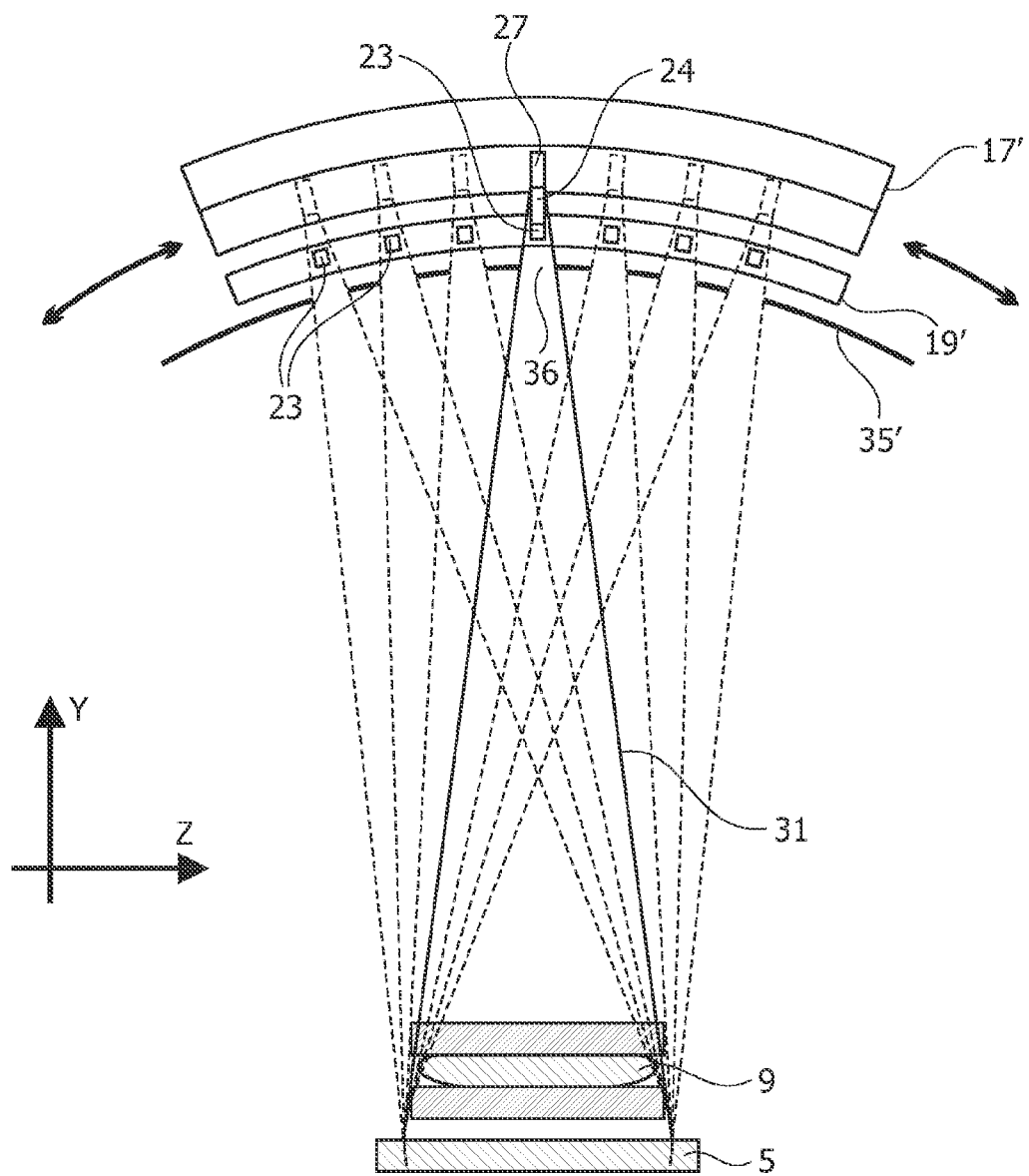
FIG. 3 shows a front view of substantial features of an X-ray imaging system with an arcuate anode arrangement according to an alternative embodiment of the invention.

FIG. 3 shows an alternative embodiment. Therein, both the electron beam source arrangement 19' as well as the anode arrangement 17' have an arcuate shape. Again, electron beams 24 may be emitted by electron emitters 23 on the electron beam source arrangement 19' accelerated towards a focal spot 27 thereby generating an X-ray beam 31 collimated by apertures 36 in an arcuate collimator 35'. A plurality of projection images may be acquired under different projection angles as indicated by the dashed lines in FIG. 3 by sequentially switching ON and OFF each of the plurality of electron emitters 23. During image acquisition, the anode arrangement 17' may be displaced in a back-and-forth movement along an arcuate path as indicated by the double arrows in FIG. 3.

Finally, some features of the distributed X-ray source and the X-ray imaging system according to embodiments of the present invention shall be summarized as follows: A new type of X-ray system for imaging applications like e.g. tomosynthesis with a multiple channel X-ray source is suggested. The X-ray system comprises a distributed X-ray source having an electron beam source arrangement with at least two electron beam emitters, preferably as many electron beam emitters as there should be projection images with one scan of the X-ray system. The electron beam emitters may offer fast switching, miniaturization and low power dissipation. Either one common anode or several separate anodes may be comprised in an anode arrangement and may be moved relative to the respective electron beams such that the resulting focal spots remain stationary in space. Switching ON and OFF of the electron beams and thus of the respectively resulting X-ray beams may be performed in order to get a sequence of projection images to compose a scan of the imaging system. The different X-ray beams may be collimated such that each "X-ray channel" may produce a projection of a same region of interest onto a detector but each time from a different angle. A digital X-ray detector may record the different projections and generate a data set for further processing. A means for processing the imaging data set may be provided in order to implement the necessary image reconstruction. The anode arrangement may comprise a direct cooling. The anode arrangement is designed and positioned such that the focal spot positions, defined by the points in space where the electron beams impinge onto the anode arrangement, may be consistent desired focal spot positions for the intended imaging application. For example, the focal spot positions could be arranged along a line or along an arc e.g. for tomosynthesis for mammography. The multiple "X-ray channels" may be switched ON and OFF alternatively with a certain desired sequence and each time the detector records one image of the desired image sequence for the application. In order to reach a required power rating for an imaging application, the anode arrangement moved relative to the electron beams in such a way that the position in space of the respective focal spots remains stationary. Therein, the motion of the anode arrangement may be a translation rather than a rotation, e.g. a back-and-forth motion, either linearly or along an arc, depending on the shape and position of the anode arrangement. If the motion of the anode arrangement is basically a translation rather than a rotation, it is possible to design the anode arrangement in such a way that the X-ray generating material is much thinner than for a conventional rotating anode, and a suitable cooling can reach very close to the focal spot in order to provide a very effective cooling, which, together with the displacement motion of the anode arrangement, may allow to reach a high power level of X-ray emission. A further possible advantage of the anode arrangement being provided with a thin sheet material may be the low weight of any moving parts. Therefore, the displacement motion of the anode arrangement does not necessarily lead to the risk of vibrations of the whole imaging system.

It should be noted that the term "comprising" does not exclude other elements or steps and that the indefinite article "a" or "an" does not exclude the plural. Also elements described in association with different embodiments may be combined. It should also be noted that reference signs in the claims shall not be construed as limiting the scope of the claims.

LIST OF REFERENCE SIGNS

1 X-ray imaging system
3 Distributed X-ray source
5 Detector
7 Examination space
9 Object
11 Plates
13 Control
15 Display
17 Anode arrangement
19 Electron beam source arrangement
21 Housing
23 Electron beam emitter
24 Electron beam
25 Switching grid
27 Focal spot
29 Sheet
31 X-ray beam
33 X-ray window
35 Collimator
36 Aperture
37 Cooling

The invention claimed is:

1. A distributed X-ray source, comprising:
an electron beam source arrangement;
an anode arrangement;
wherein the electron beam source arrangement is adapted to emit electron beams towards at least two locally distinct focal spots on the anode arrangement for acquiring at least two projection images, respectively, of an object of interest; and
wherein the X-ray source is adapted for displacing the anode arrangement in a non-rotational movement with respect to the electron beam source arrangement along a path of the anode arrangement during a time period for acquiring a respective projection image of the at least two projection images, wherein the path of the anode arrangement includes the at least two locally distinct focal spots, and wherein displacing the anode arrangement further comprises displacing along the path in a back-and-forth movement that includes a first displacement direction along the path and a second displacement direction, opposite the first displacement direction along the path.

2. The distributed X-ray source of claim 1, wherein the X-ray source is adapted for displacing the anode arrangement with respect to the electron beam source arrangement in a way such that during the displacing movement a position of the focal spots remains stationary.

3. The distributed X-ray source of claim 1, wherein the X-ray source is adapted for displacing the anode arrangement with respect to the electron beam source arrangement in the back-and-forth movement along one of a linear path, an arcuate path and a curvilinear path.

4. The distributed X-ray source of claim 1, wherein a distance between adjacent focal spots is at least 5 mm.

5. The distributed X-ray source of claim 1, wherein the electron beam source arrangement is adapted for fast switching ON and OFF emitted electron beams.

6. The distributed X-ray source of claim 1, wherein the electron beam source arrangement comprises a plurality of electron beam emitters, each emitter being adapted for emitting an electron beam towards one associated focal spot on the anode arrangement.

7. The distributed X-ray source of claim 1, wherein the distributed X-ray source is adapted for switching ON and OFF X-ray beams emitted from different focal spots independently from each other.

8. The distributed X-ray source of claim 1, wherein the electron beam source arrangement is provided with at least one of a cold field emission cathode, a photoelectric cathode and a low work function cathode.

9. The distributed X-ray source of claim 1, wherein the anode arrangement is provided with a sheet such that electrons emitted from the electron source arrangement impinge on one surface of the sheet and wherein the anode arrangement is provided with an active cooling arranged on an opposite side of the sheet.

10. An X-ray imaging system, comprising:
a distributed X-ray source according to claim 1 arranged on a first side of an examination space;
a detector arranged on a second side opposite to the first side of the examination space;
wherein the distributed X-ray source is adapted such that X-rays emitted from each of the focal spots cross the examination space at a different angle.

11. The X-ray imaging system of claim 10, further comprising a collimator for collimating X-rays emitted from at least one of the focal spots into X-ray channels for projecting a region of interest in the examination space onto the detector.

12. The X-ray imaging system of claim 10, wherein the X-ray imaging system is adapted to emit X-rays sequentially from the focal spots for projecting a region of interest in the examination space under different angles onto the detector and to acquire a plurality of respective projection images with the detector.

13. The X-ray imaging system of claim 12, wherein the X-ray imaging system is adapted to provide a 3-dimensional image of the region of interest based on the acquired projection images.

14. A medical imaging system comprising the X-ray imaging system of claim 10, wherein the medical imaging system is adapted for tomosynthesis.

* * * * *